United States Patent
Flohr et al.

(10) Patent No.: US 7,838,569 B2
(45) Date of Patent: Nov. 23, 2010

(54) METHOD OF SURFACE CROSS-LINKING SUPERABSORBENT POLYMER PARTICLES USING ULTRAVIOLET RADIATION AND BRONSTED ACIDS

(75) Inventors: Andreas Flohr, Kronberg (DE); Torsten Lindner, Kronberg (DE); Yoshiro Mitsukami, Hyogo (JP)

(73) Assignee: Nippon Shokubai Co., Ltd, Osaka (JP)

( * ) Notice: Subject to any disclaimer, the term of this patent is extended or adjusted under 35 U.S.C. 154(b) by 11 days.

(21) Appl. No.: 12/064,706

(22) PCT Filed: Aug. 22, 2006

(86) PCT No.: PCT/JP2006/316792

§ 371 (c)(1),
(2), (4) Date: Feb. 25, 2008

(87) PCT Pub. No.: WO2007/023978

PCT Pub. Date: Mar. 1, 2007

(65) Prior Publication Data
US 2009/0131633 A1    May 21, 2009

(30) Foreign Application Priority Data
Aug. 23, 2005 (EP) .................................. 05018264

(51) Int. Cl.
*C08F 2/48* (2006.01)
(52) U.S. Cl. ...................... 522/4; 522/1; 522/5; 522/6; 522/71; 528/480; 528/487; 528/490; 508/459; 508/468; 525/329.4
(58) Field of Classification Search ............. 526/317.1, 526/318; 525/384, 329.4, 330.1, 330.6; 428/403, 428/323, 327, 407; 508/459, 468; 528/480, 528/487, 490; 522/1, 5, 6, 71
See application file for complete search history.

(56) References Cited

U.S. PATENT DOCUMENTS

| | | | | |
|---|---|---|---|---|
| 5,610,208 | A * | 3/1997 | Dairoku et al. | ............. 525/384 |
| 7,166,356 | B2 | 1/2007 | Flohr | |
| 7,201,941 | B2 | 4/2007 | Irie et al. | |
| 2003/0069359 | A1* | 4/2003 | Torii et al. | ................. 525/178 |
| 2005/0032936 | A1* | 2/2005 | Flohr | ........................ 523/205 |
| 2005/0203474 | A1* | 9/2005 | Flohr | ........................ 604/368 |
| 2006/0020053 | A1 | 1/2006 | Flohr et al. | |
| 2006/0128902 | A1 | 6/2006 | Flohr et al. | |
| 2007/0048516 | A1 | 3/2007 | Flohr et al. | |
| 2007/0048517 | A1 | 3/2007 | Flohr et al. | |
| 2007/0048518 | A1 | 3/2007 | Flohr et al. | |

FOREIGN PATENT DOCUMENTS

| | | |
|---|---|---|
| EP | 1504771 | 2/2005 |
| EP | 1504772 | 2/2005 |
| EP | 1506788 | 2/2005 |
| EP | 1568385 | 8/2005 |
| EP | 1618900 | 1/2006 |
| EP | 1621561 | 2/2006 |
| EP | 1629854 | 3/2006 |
| EP | 1669394 | 6/2006 |
| EP | 1824910 | 6/2006 |
| EP | 1838766 | 6/2006 |
| JP | A-63-043930 | 2/1988 |
| JP | A-63-099211 | 4/1988 |
| JP | A-2005-200630 | 7/2005 |
| JP | A-2006-169267 | 6/2006 |
| WO | WO2005/082429 | 9/2005 |
| WO | WO2006/062253 | 6/2006 |
| WO | WO2006/062258 | 6/2006 |
| WO | WO2007/024926 | 3/2007 |
| WO | WO2007/024927 | 3/2007 |
| WO | WO2007/024939 | 3/2007 |

OTHER PUBLICATIONS

International Preliminary Report on Patentability received in International Application No. PCT/JP2006/316792 dated Mar. 6, 2008.
Supplementary European Search Report, from corresponding EP application 06783074.
IUPAC, IUPAC Compendium of Chemcial Terminology, $2^{nd}$ Edition, HTTP://WWW.IUPAC.ORG/GOLDBOOK/B00744.PDF, XP002365877 (1997).

* cited by examiner

*Primary Examiner*—Ling-Siu Choi
*Assistant Examiner*—Frances Tischler
(74) *Attorney, Agent, or Firm*—Occhiuti Rohlicek & Tsao LLP

(57) ABSTRACT

The present invention relates to a method of surface cross-linking superabsorbent polymer particles using UV irradiation. The superabsorbent polymer particles for use in the method of the present invention have a relatively high degree of neutralization. Bronsted acids are selectively applied onto the surface of the superabsorbent polymer particles to selectively facilitate a relatively high number of protonated carboxyl groups at the surface of the superabsorbent polymer particles while the relatively high degree of neutralization in the core of the superabsorbent polymer particles remains substantially unaffected.

15 Claims, No Drawings

METHOD OF SURFACE CROSS-LINKING SUPERABSORBENT POLYMER PARTICLES USING ULTRAVIOLET RADIATION AND BRONSTED ACIDS

CROSS-REFERENCE TO RELATED APPLICATIONS

This application is the National Stage of International Application No. PCT/JP2006/316792, filed on Aug. 22, 2006, which claims the priority of European Application No. 05018264.1, filed on Aug. 23, 2005. The contents of both applications are hereby incorporated by reference in their entirety.

TECHNICAL FIELD

The present invention relates to a method for making surface-cross-linked superabsorbent polymer (SAP) particles, using ultraviolet (UV) radiation. The method uses SAP particles with a relatively high degree of neutralization and further applies Brønsted acids.

BACKGROUND ART

Superabsorbent polymers (SAPs) are well known in the art. They are commonly applied in absorbent articles, such as diapers, training pants, adult incontinence products and feminine care products to increase the absorbent capacity of such products while reducing their overall bulk. SAPs are capable of absorbing and retaining amounts of aqueous fluids equivalent to many times their own weight.

Commercial production of SAPs began in Japan in 1978. The early superabsorbent was a cross-linked starch-g-polyacrylate. Partially neutralized polyacrylic acid eventually replaced earlier superabsorbents in the commercial production of SAPs, and has become the primary polymer in SAPs. SAPs are often applied in form of small particles. They generally consist of a partially neutralized lightly cross-linked polymer network, which is hydrophilic and permits swelling of the network once submerged in water or an aqueous solution such as physiological saline. The cross-links between the polymer chains assure that the SAP does not dissolve in water.

After absorption of an aqueous solution, swollen SAP particles become very soft and deform easily. Upon deformation the void spaces between the SAP particles are blocked, which drastically increases the flow resistance for liquids. This is generally referred to as "gel-blocking". In gel blocking situations liquid can move through the swollen SAP particles only by diffusion, which is much slower than flow in the interstices between the SAP particles.

One commonly applied way to reduce gel blocking is to make the particles stiffer, which enables the swollen SAP particle's to retain their original shape thus creating or maintaining void spaces between the particles. A well-known method to increase stiffness is to cross-link the carboxyl groups exposed on the surface of the SAP particles. This method is commonly referred to as surface cross-linking.

The art refers e.g. to surface cross-linked and surfactant coated absorbent resin particles and a method of their preparation. The surface cross-linking agent can be a polyhydroxyl compound comprising at least two hydroxyl groups, which react with the carboxyl groups on the surface of the SAP particles. In some art, surface cross-linking is carried out at temperatures of 150° C. or above.

More recently the use of an oxetane compound and/or an imidazolidinone compound for use as surface cross-linking agent has been disclosed. The surface cross-linking reaction can be carried out under heat, wherein the temperature is preferably in the range of 60° C. to 250° C. Alternatively, the surface cross-linking reaction can also be achieved by a photo-irradiation treatment, preferably using ultraviolet rays.

A drawback of the commercial surface cross-linking process described above is that it takes relatively long, commonly at least about 30 min. However, the more time is required for the surface cross-linking process, the more surface cross-linking agent will penetrate into the SAP particles, resulting in increased cross-linking inside the particles, which has a negative impact on the capacity of the SAP particles. Therefore, it is desirable to have short process times for surface cross-linking. Furthermore, short process times are also desirable with respect to an overall economic SAP particle manufacturing process.

Another drawback of common surface cross-linking processes is, that they take place only under relatively high temperatures, often around 150° C. or above. At these temperatures, not only the surface cross-linker reacts with the carboxyl groups of the polymer, but also other reactions are activated, such as anhydride-formation of neighbored carboxyl groups within or between the polymer chains, and dimer cleavage of acrylic acid dimers incorporated in the SAP particles. Those side reactions also affect the core, decreasing the capacity of the SAP particles. In addition, exposure to elevated temperatures can lead to color degradation of the SAP particles. Therefore, these side reactions are generally undesirable.

The use of acids for the production of water-absorbent agents is disclosed in U.S. Pat. No. 5,610,208. The patent refers to a method for producing water-absorbent agents which comprises mixing a water-absorbent resin containing a carboxyl group with an additive of at least one member selected from the group consisting of inorganic acids, organic acids, and polyamino acids and a cross-linking agent capable of reacting with the carboxyl group. The mixture is subjected to a heat treatment at a temperature in the range of from 100° C. to 230° C.

SAPs known in the art are typically partially neutralized, e.g. with sodium hydroxide. However, neutralization has to be carefully balanced with the need for surface cross-linking: The surface cross-linking agents known in the art react with free carboxyl groups comprised by the polymer chains at relatively high speed but react with a neutralized carboxyl groups only very slowly. Thus, a given carboxyl groups can either be applied for surface cross-linking or for neutralization, but not for both. Surface cross-linking agents known in the art preferably react with the carboxyl groups, they do not react with aliphatic groups.

In the process of making SAP particles, neutralization of free carboxyl groups typically comes first, before surface cross-linking takes place. Indeed, the neutralization step is often carried out in the very beginning of the process, before the monomers are polymerized and cross-linked to form the SAP. Such a process is named 'pre-neutralization process'. Alternatively, the SAP can be neutralized during polymerization or after polymerization ('post-neutralization'). Furthermore, a combination of these alternatives is also possible.

The overall number of free carboxyl groups on the outer surface of the SAP particles is not only limited by the foregoing neutralization but the free carboxyl groups are also believed to be not homogeneously distributed. Hence, it is currently difficult to obtain SAP particles with evenly distributed surface cross-linking. On the contrary, often SAP particles have regions of rather dense surface cross-linking, i.e. with a relatively high number of surface cross-links, and regions of sparsely surface cross-linking. This inhomogeneity has a negative impact on the desired overall stiffness of the SAP particles.

It is therefore an objective of the present invention to provide a method of making SAP particles with evenly distributed, homogenous surface cross-linking while using SAP particles having a high degree of neutralization.

It is a further objective of the present invention to provide an economic method of surface cross-linking SAP particles Moreover, it is difficult to obtain SAP particles having both, sufficient stiffness to avoid gel blocking (sometimes referred to as "gel strength") and sufficient swelling capacity (sometimes referred to as "gel volume"). Typically, increasing the gel strength of the SAP particles has a negative impact on the gel volume and vice versa.

Thus, it is a further objective of the present invention to restrict the surface cross-links to the very surface of the SAP particles in order to minimize the decrease in capacity. Thus, the core of the SAP particles should not be considerably affected and the additional cross-links introduced in the core should be kept to a minimum.

Moreover, it is an objective of the present invention to provide a method of surface cross-linking SAP particles, which can be carried out quickly to increase the efficiency of the method.

A still further objective of the present invention is to provide a method of surface cross-linking SAP particles, which can be carried out at moderate temperatures in order to reduce undesired side reactions, such as anhydride-formation and dimer cleavage.

SUMMARY OF THE INVENTION

The present invention relates to a method of surface cross-linking superabsorbent polymer particles which comprises the steps of
a) providing superabsorbent polymer particles having a surface and a core and having a degree of neutralization of more than 0.60 mol-%;
b) applying one or more Brønsted acids onto the surface of the superabsorbent polymer particles; and either
c1) exposing the superabsorbent polymer particles to irradiation with vacuum UV radiation having a wavelength from 100 nm to 200 nm or
c2) exposing the superabsorbent polymer particles to irradiation with UV radiation having a wavelength from 201 nm to 400 nm and wherein further to the Brønsted acids, radical former molecules are applied to the surface of the superabsorbent polymer particles.

DISCLOSURE OF INVENTION

The SAPs according to the present invention preferably comprise a homo-polymer of partially neutralized $\alpha,\beta$-unsaturated carboxylic acid or a copolymer of partially neutralized $\alpha,\beta$-unsaturated carboxylic acid copolymerized with a monomer co-polymerizable therewith. Furthermore, the homo-polymer or copolymer preferably comprised by the SAP comprises aliphatic groups, wherein at least some of the aliphatic groups are at least partially comprised by the surface of the SAP particles.

SAPs are available in a variety of chemical forms, including substituted and unsubstituted natural and synthetic polymers, such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, SAPs useful herein have a multiplicity of anionic, functional groups, such as sulfonic acid, and more typically carboxyl groups. Examples of polymers suitable for use herein include those, which are prepared from polymerizable, unsaturated, acid-containing monomers. Thus, such monomers include the olefinically unsaturated acids and anhydrides that contain at least one carbon-to-carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing SAPs. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 and in U.S. Pat. No. 4,062,817.

Olefinically unsaturated carboxylic acid and carboxylic acid anhydride monomers include the (meth) acrylic acids typified by acrylic acid itself, methacrylic acid, ethacrylic acid, $\alpha$-chloroacrylic acid, $\alpha$-cyanoacrylic acid, $\beta$-methylacrylic acid (crotonic acid), $\alpha$-phenylacrylic acid, $\beta$-acryloxypropionic acid, sorbic acid, $\alpha$-chlorosorbic acid, angelic acid, cinnamic acid, p-chlorocinnamic acid, $\beta$-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred SAPs according to the present invention contain carboxyl groups. These polymers comprise hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network cross-linked polymers of any of the foregoing copolymers, partially neutralized polyacrylic acid, and slightly network cross-linked polymers of partially neutralized polyacrylic acid, partially neutralized polymethacrylic acid, and slightly network cross-linked polymers of partially neutralized polymethacrylic acid. These polymers can be used either solely or in the form of a mixture of two or more different polymers, that when used as mixtures, individually do not have to be partially neutralized, whereas the resulting copolymer has to be. Examples of these polymer materials are disclosed in U.S. Pat. Nos. 3,661,875, 4,076,663, 4,093,776, 4,666,983, and 4,734,478.

Most preferred polymer materials for use herein are slightly network cross-linked polymers of partially neutralized polyacrylic acids, slightly network cross-linked polymers of partially neutralized polymethacrylic acids, their copolymers and starch derivatives thereof. Most preferably, SAPs comprise partially neutralized, slightly network cross-linked, polyacrylic acid (i.e. poly (sodium acrylate/acrylic acid)). The SAPs for use in the present invention are at least 60 mol-% to 95 mol-%, more preferably at least 65 mol-% to 95 mol-% even more preferably at least 70 mol-% to 95 mol-% and even more preferably from 75 mol-% to 95 mol-% neutralized. Network cross-linking renders the polymer substantially water-insoluble and, in part, determines the absorptive capacity of the hydrogel-forming absorbent polymers. Processes for network cross-linking these polymers and typical network cross-linking agents are described in greater detail in U.S. Pat. No. 4,076,663.

A suitable method for polymerizing α,β-unsaturated carboxylic acid monomers is aqueous solution polymerization, which is well known in the art. An aqueous solution comprising α,β-unsaturated carboxylic acid monomers and polymerization initiator is subjected to a polymerization reaction. The aqueous solution may also comprise further monomers, which are co-polymerizable with α,β-unsaturated carboxylic acid monomers. At least the α,β-unsaturated carboxylic acid has to be partially neutralized, either prior to polymerization of the monomers, during polymerization or post polymerization.

The monomers in aqueous solution are polymerized by standard free radical techniques, commonly by using a photoinitiator for activation, such as ultraviolet (UV) light activation. Alternatively, a redox initiator may be used. In this case, however, increased temperatures are necessary.

The water-absorbent resin will preferably be lightly cross-linked to render it water-insoluble. The desired cross-linked structure may be obtained by the co-polymerization of the selected water-soluble monomer and a cross-linking agent possessing at least two polymerizable double bonds in the molecular unit. The cross-linking agent is present in an amount effective to cross-link the water-soluble polymer. The preferred amount of cross-linking agent is determined by the desired degree of absorption capacity and the desired strength to retain the absorbed fluid, that is, the desired absorption under load. Typically, the cross-linking agent is used in amounts ranging from 0.0005 to 5 parts by weight per 100 parts by weight of monomers (including α, β-unsaturated carboxylic acid monomers and possible co-monomers) used. If an amount over 5 parts by weight of cross-linking agent per 100 parts is used, the resulting polymer has a too high cross-linking density and exhibits reduced absorption capacity and increased strength to retain the absorbed fluid. If the cross-linking agent is used in an amount less than 0.0005 parts by weight per 100 parts, the polymer has a too low cross-linking density and when contacted with the fluid to be absorbed becomes rather sticky, water-soluble and exhibits a low absorption performance, particularly under load. The cross-linking agent will typically be soluble in the aqueous solution.

Alternatively to co-polymerizing the cross-linking agent with the monomers, it is also possible to cross-link the polymer chains in a separate process step after polymerization.

After polymerization, cross-linking and partial neutralization, the wet SAPs are dehydrated (i.e. dried) to obtain dry SAPs. The dehydration step can be performed by heating the viscous SAPs to a temperature of about 120° C. for about 1 or 2 hours in a forced-air oven or by heating the viscous SAPs overnight at a temperature of about 60° C. The content of residual water in the SAP after drying predominantly depends on drying time and temperature. According to the present invention, "dry SAP" refers to SAP with a residual water content of from 0.5% by weight of dry SAP up to 50% by weight of dry SAP, preferably, from 0.5%-45% by weight of dry SAP, more preferably 0.5%-30%, even more preferred 0.5%-15% and most preferred 0.5%-5%. If not explicitly said to be otherwise, in the following the term "SAP particles" refers to dry SAP particles.

The SAPs can be transferred into particles of numerous shapes. The term "particles" refers to granules, fibers, flakes, spheres, powders, platelets and other shapes and forms known to persons skilled in the art of SAPs. E.g. the particles can be in the form of granules or beads, having a particle size of about 10 μm to 1000 μm, preferably about 100 μm to 1000 μm. In another embodiment, the SAPs can be in the shape of fibers, i.e. elongated, acicular SAP particles. In those embodiments, the SAP fibers have a minor dimension (i.e. diameter of the fiber) of less than about 1 mm, usually less than about 500 μm, and preferably less than 250 μm down to 50 μm. The length of the fibers is preferably about 3 mm to about 100 mm. Though less preferred for use in the present invention, the fibers can also be in the form of a long filament that can be woven.

The SAP particles of the present invention have a core and a surface. According to the present invention the dry SAP particles undergo a surface cross-linking process step, i.e. they are cross-linked in their surface while the number of cross-links in the core of the particle is not substantially increased by the method of the invention.

The term "surface" describes the outer-facing boundaries of the particle. For porous SAP particles, exposed internal surfaces may also belong to the surface. For the present invention, "surface" of the SAP particles refers to the complete and continuous outwardly facing 6% volume of the dry SAP particle, whereas "core" refers to 94% of the volume and comprises the inner regions of the dry SAP particle.

Surface cross-linked SAP particles are well known in the art. In surface cross-linking methods of the prior art, a surface cross-linker is applied to the surface of the SAP particles. In a surface cross-linked SAP particle the level of cross-links in the surface of the SAP particle is considerably higher than the level of cross-links in the core of the SAP particle.

Commonly applied surface cross-linkers are thermally activatable surface cross-linkers. The term "thermally activatable surface cross-linkers" refers to surface cross-linkers, which only react upon exposure to increased temperatures, typically around 150° C. Thermally activatable surface cross-linkers known in the prior art are e.g. di- or polyfunctional agents that are capable of building additional cross-links between the polymer chains of the SAPs. Typical thermally activatable surface cross-linkers include, e.g., di- or polyhydric alcohols, or derivatives thereof, capable of forming di- or polyhydric alcohols. Representatives of such agents are alkylene carbonates, ketales, and di- or polyglycidylethers. Moreover, (poly)glycidyl ethers, haloepoxy compounds, polyaldehydes, polyoles and polyamines are also well known thermally activatable surface cross-linkers. The cross-linking is for example formed by an esterification reaction between a carboxyl group (comprised by the polymer) and a hydroxyl group (comprised by the surface cross-linker). As typically a relatively big part of the carboxyl groups of the polymer chain is neutralized prior to the polymerization step, commonly only few carboxyl groups are available for this surface cross-linking process known in the art. E.g. in a 70 mol-% percent neutralized polymer only 3 out of 10 carboxylic groups are available for covalent surface cross-linking.

The method of the present invention is used for surface cross-linking of SAP particles. Hence, the polymer chains comprised by the SAP particles already have been cross-linked by a cross-linker known in the art, comprising at least two polymerizable double bonds in the molecule unit.

In the method of the present invention, direct covalent bonds between carbon atoms comprised in the backbone of different polymer chains are formed in the surface of the SAP particles.

A "direct covalent bond" according to the present invention is a covalent bond wherein polymer chains are bound to each other only via a covalent bond with no intermediate atoms, such as atoms comprised by a cross-linking molecule. In contrast, known cross-linking reactions between polymer chains always result in covalent bonds between these polymer chains, wherein the reaction product of the cross-linking molecule is built in between the polymer chains. Thus, known surface cross-linking reactions do not result in a direct covalent bond but in an indirect covalent bond comprising the reaction product of the cross-linking molecule. The direct covalent bond is formed between a carbon atom in the backbone of a first polymer chain and a carbon atom in the backbone of a second polymer chain. The bonds are formed intra-particulate within the SAP particle, more specifically, they are formed in the surface of the SAP particles, while the core of the SAP particles is substantially free of such direct covalent bonds.

The "backbone" of a polymer chain refers to those carbon atoms which immediately form the polymer chain. Principally, if a reaction resulted in the removal of a carbon atom, which is part of the polymer chain backbone, this reaction would also result in the break of the polymer chain on the position, where this carbon atom had previously been built into the polymer chain.

Optionally, surface cross-linking molecules may also be used for the method of the present invention. In such embodiments wherein surface cross-linking molecules are added to the SAP particles, additional covalent bonds are formed between the polymer chains comprised in the surface of the SAP particles. These additional covalent bonds comprise the reaction product of said surface cross-linking molecules.

The cross-linking of different polymer chains of the present invention is not intended to bond different SAP particles to each other. Thus, the method of the present invention does not lead to any appreciable inter-particulate bonds between different SAP particles but only results in intra-particulate direct covalent bonds within an SAP particle. If present, such inter-particulate direct covalent bonds would hence require additional inter-particulate cross-linking materials.

The method of the present invention which directly bonds polymer chains to each other by a covalent bond between two carbon atoms can be applied for surface cross-linking SAP particles instead of or additional to conventional surface cross-linking.

Radiation Activatable Radical Former Molecules

If UV radiation having a wavelength from 100 nm to 200 nm (vacuum UV, hereinafter referred to as VUV) is used, for the method of the present invention, radiation activatable radical former molecules may optionally be applied to increase the efficiency of the surface cross-linking. However, the use of such radical formers is not mandatory for VUV and may, indeed, be omitted to reduce costs, as the radical formers may substantially add to the total costs of the surface cross-linking method. Due to the use of VUV, the radical formers are not necessarily required to initiate the surface cross-linking reaction.

If UV radiation having a wavelength from 201 nm to 400 nm is used for the method of the present invention, radical former molecules have to be applied as the surface cross-linking reaction, which is a radical reaction, cannot be initiated otherwise.

The radiation activatable radical former molecules (hereinafter called radical formers) are able to form carbon centered radicals located in the polymer backbone of polymer chains comprised in the surface of the SAP particles. This reaction takes place upon UV irradiation. Two of these carbon centered radicals comprised in different polymer chains are able to react with each other and thereby form a direct covalent bond between the polymer chains.

Upon irradiation, some of the radical formers form, in a first step, an intermediate radical, which is typically oxygen-centered, and which may, in a second step, react with a carbon atom comprised in the polymer backbone in the surface of the SAP particle to form a carbon centered radical in the polymer backbone.

In principle, any photo-initiator which is typically used to start the polymerization of vinyl monomers can be applied as a radical former for surface cross-linking according to the present invention. Such photoinitiators typically serve to trigger radical chain polymerizations of vinyl monomers. It is believed that the reactive intermediate species, which is formed upon irradiation of the photoinitiator with UV radiation, is capable of abstracting hydrogen atoms from C—H bonds of C atoms comprised by the polymer backbone of polymer chains in the surface of the SAP particle (therewith initiating the cross-linking according to the present invention).

Most preferably, the radiation activatable radical former molecule comprises a peroxo bridge (O—O), which is homolytically cleaved upon UV irradiation (so-called photo-fragmentation).

However, reactive intermediate species can also be ketones which—upon UV irradiation—have been transferred into short-lived, a so-called excited triplet state. The keton in the triplet-state is also capable of abstracting hydrogen from C—H bonds of C atoms comprised by the polymer backbone whereby the ketone is converted into an alcohol (so-called photo reduction).

It is highly preferred that the radical former of the present invention is water soluble. The water soluble radical former should exhibit a solubility in water of at least 1 wt %, preferably at least 5 wt % at most preferred at least 10 wt % at 25° C.

Radical formers, which are not initially water soluble, can be rendered water soluble by derivatization, e.g. by introducing a charged group into the molecular structure, such as carboxylate or ammonium. As an example, benzophenone can be easily derivatized into benzoyl benzoic acid. However, it is preferred that the radical formers are inherently water soluble, i.e. the introduction of a functional group is not required. Typical, inherently water soluble radiation activatable radical formers are peroxides like alkali-metal or other inorganic peroxodisulfates, or derivatized organic peroxodisulfates. Water-soluble azo-initiators can be used as well (such as the commercially available V-50 or VA-086, Wako Specialty Chemicals). Inorganic peroxides typically fulfill the requirement of water solubility, while organic compounds typically require derivatization. The most preferred water-soluble radical former is sodium peroxodisulfate.

The advantage of providing the radical former in an aqueous solution (and hence, the advantage of using a water-soluble radical former) is two-fold: On the one hand, the aqueous solution facilitates an efficient wetting of the SAP particle surface. Thus, the radical former molecules are actually transported into the particle surface, where they initiate the surface cross-linking reaction.

On the other hand, efficient wetting of the SAP particle surface enhances the chain mobility of the polymer chains comprised in the surface of the SAP particles. This facilitates the bimolecular reaction between the carbon atoms comprised in the polymer backbone and the reactive intermediate species, into which the radical former is transformed upon irradiation. This effect is particularly advantageous for SAP particles comprised of poly(meth)acrylic acid, which are in fact the most widely used SAP particles of today. Polyacrylic acid possesses a glass transition temperature of 106° C. and the sodium salt of polyacrylic acid, at a neutralization degree of 100 mol-%, has a glass transition temperature of above 200° C. while the surface cross-linking of the present invention is typically carried but at temperatures below 100° C. In the presence of water, the glass transition temperature of partly neutralized polyacrylic acid can be significantly decreased. E.g., the glass transition temperature of a 65 mol-% neutralized sodium polyacrylate can be reduced from ca. 150° C. in the presence of 5 wt % water to below room temperature in the presence of 35 wt % water. However, to make use of this effect, the actual local water concentration directly in the surface of the SAP particle is important.

To ensure that the cross-linking of the present invention is actually restricted to the surface of the SAP particles, the water should be prevented from evenly distributing throughout the whole particle volume via diffusion. Therefore, the UV irradiation step should follow not later than one hour after the aqueous solution comprising the radical former has been applied onto the SAP particles, more preferably not later than 10 minutes and most preferably not later than 1 minute.

Water-soluble radical formers are highly preferred, as organic solvents are typically more expensive than water and are also more problematic from an environmental standpoint. However, organic radial formers which have not been rendered water-soluble via the above-described derivitization may also be used and can be applied in an organic solvent rather than in water. Examples are benzophenone or any other suitable ketone which is known to undergo photoreduction when irradiated with UV radiation. A further example is dibenzoyl peroxide or any other organic peroxide which is known to undergo photo fragmentation when irradiated with UV radiation.

In the method of the present invention, the radical former is preferably applied in amounts of less than 25% by weight of SAP particles, more preferably in amounts of less than 15%, and most preferably in amounts from 1% to 5%. The radical former is typically applied in aqueous solution. Alternatively, but less preferred, the radical former and the water can be added in two steps, but both have to be present on the surface during irradiation. The amount of water is preferably less than 25% by weight of SAP particles, more preferably less than 15% and most preferably from 5% to 10%. For economic reasons, it is preferred to keep the amount of water added as low as possible to shorten or entirely avoid a drying step after the surface cross-linking.

Surface Cross-linking Molecules

The surface cross-linking molecule is any compound having at least two functional groups which can react with the aforementioned carbon-centered radicals located in the backbone of the polymer chains comprised in the surface of the SAP particles. Upon reaction of the functional group in the surface cross-linking molecule with the carbon-centered radical, a new covalent bond is formed, grafting the cross-linking molecule onto the polymer backbone.

The functional groups of the surface cross-linking molecules are preferably C=C double bonds. More preferably, a cross-linking molecule comprises more than two C=C double bonds. Alternatively, the functional groups can also be CH—X moieties, with X being a hetero atom. A preferred example of a CH—X moiety is an ether, CH—O—R, with R being an alkyl residue.

Preferred cross-linking molecules of the present invention are polyfunctional allyl and acryl compounds, such as triallyl cyanurate, triallyl isocyanurate, trimethylpropane tricrylate or other triacrylate esters, pentaerythritol triallyl ether, pentaerythritol tetraallyl ether, butanediol diacrylate, pentaerythritol tetraacrylate, tetra allylorthosilicate, di-pentaerythritol pentaacyralate, di-pentaerythritol hexaacyralate, ethyleneglycol diacrylate, ethyleneglycol dimethacrylate, tetra allyloxy ethane, diallyl phthalate, diethyleneglycol diacrylate, allylmethacrylate, 1,1,1-trimethylolpropane triacrylate, triallyl citrate, or triallyl amine.

Alternatively, the cross-linking molecules are selected from the group consisting of squalene, N,N' methylenebisacrylamide, icosa-pentaenic acid, sorbic acid or vinyl terminated silicones.

Compounds with allylic double bonds are generally more preferred than compounds with acrylic double bonds. The most preferred cross-linking molecule of the present invention is diallyl dimethyl ammonium chloride.

If surface cross-linking molecules are applied, they should be added e.g. by spray application in a solution with an inert solvent (that can be optionally evaporated) before the SAP particles undergo UV irradiation. The surface cross-linking molecules can be applied in an organic solvent like dichloromethane which is evaporated directly after application. In embodiments, wherein the SAP particles are moisturized, the surface cross-linking molecules can also be applied together with the water as a suspension or, if the surface cross-linking molecules are water soluble, as a solution.

Moreover, in embodiments wherein surface cross-linking molecules are applied together with radical formers, the molar ratio of surface cross-linking molecules to radical former is preferably in the range of from 0.2 to 5, more preferably from 0.33 to 3 and most preferred from 1 to 3.

In embodiments, wherein only surface cross-linking molecules are used without additional use of radical formers (only applicable for VUV irradiation), the surface cross-linking molecules are preferably applied in a concentration from 0.1% to 10% by weight of dry SAP particles, more preferably from 1% to 5%.

The surface cross-linking compound is preferably water-soluble, so that it can be applied with the aqueous solution comprising the radical former (optional for use of VUV). If a less preferred water-insoluble surface cross-linking molecules is applied, it may be emulsified or suspended in the aqueous solution comprising the radical former or be applied separately. Water-insoluble surface cross-linking molecules can also be applied in an organic solvent like dichloromethane which is evaporated directly after application.

The surface cross-linking molecules and/or the radical former may be sprayed onto the SAP particles by means of a fluidized-bed spraying chamber. Simultaneously IR-irradiation may be applied to accomplish drying. Instead or in combination with IR-light, any conventional drying equipment can be used for drying. However, in certain embodiments of the present invention little or no drying is required, e.g. in cases, where only small amounts of surface cross-linking molecules and/or the radical former are applied, dissolved in small amounts of solution.

According to the method of the present invention, the surface cross-linking molecules and/or the radical formers are always applied onto the SAP particles prior to UV irradiation or simultaneously with UV irradiation.

Reaction Mechanism without Radical Formers and without Surface Cross-linking Molecules (Applicable for Use of VUV Only)

Several mechanisms, can be distinguished that contribute to the formation of the intermediate carbon-centred radicals. To some degree, those mechanisms may take place simultaneously.

Upon irradiation with UV having a wavelength from 100 nm to 200 nm (vacuum UV, in the following called VUV), hydroxyl radicals are generated from water molecules via homolytic cleavage of O—H bonds. Those highly reactive, short-lived species are capable of abstracting hydrogen atoms from the carbon-hydrogen bonds (C—H bonds) comprised in the backbone of the polymer chains in the surface of the SAP particles, resulting in the formation of said carbon-centred radicals:

Principally, it is also possible that instead of abstracting a hydrogen atom from a carbon-hydrogen bond comprised in the backbone of the polymer chain, a complete carboxyl group is abstracted from the polymer chain (decarboxylation). As a result of this reaction, a carbon-centred radical is formed in the backbone of a polymer chain comprised in the surface of the SAP particle.

The water molecules can e.g. be the residual water molecules comprised within the dry SAP particles but can also be provided by slightly moisturizing the SAP particles via a spray application or, preferably, as water vapor. Moisturizing may e.g. be advisable if SAP particles with relatively low residual water contents (below 0.5% by weight of the dry SAP particles) are used.

Reaction Mechanism with Radical Formers (Optional for Use of VUV) and with Optional Surface Cross-linking Molecules:

The radical former molecules undergoing photo-fragmentation comprise a labile bond. Upon UV irradiation, the labile bond breaks, whereby two radicals ($R_a$. and $R_b$.) are formed.

This homolytic cleavage may result in two identical radicals, if the labile bond comprised by the radical former molecule (so-called precursor molecule) divides the molecule into two identical parts. Alternatively, the homolytic cleavage may result in two different radicals.

The radicals, which have been formed, can now react with an aliphatic C—H group comprised in the backbone of the polymer chains in the surface of the SAP particle forming a carbon-centered radical in the polymer backbone. Two such carbon-centered radicals can react with each other to form a direct covalent bond between the carbon atoms comprised in the polymer backbone.

Again, it is principally also possible that instead of abstracting a hydrogen atom from a carbon-hydrogen bond comprised in the backbone of the polymer chain, a complete carboxyl group is abstracted from the polymer chain (decarboxylation). As a result of this reaction, a carbon-centred radical is formed in the backbone of a polymer chain comprised in the surface of the SAP particle.

Optionally, surface cross-linking molecules may be additionally used for the method of the present invention. In such embodiments, the radicals formed from the radical former molecule, can react with one of the C=C double bonds comprised by the cross-linking molecule to form a radical consisting of the reaction product of the cross-linking molecule and the initial radical.

The carbon-centered radical within the polymer chain segment can react with this radical. The reaction product of this reaction is a polymer chain wherein the reaction products of the radical former molecule and the cross-linking molecule are covalently bound to a carbon atom of the polymer backbone.

Thereafter, the radicals formed from the radical former molecule, can react with the second of the C=C double bonds of the cross-linking molecule.

To form the cross-link between two polymer chains, the carbon-centered radical combines with another carbon centered radical comprised in another polymer chain in the surface of the same SAP particle.

Hence, contrary to the reaction described above for VUV only, wherein no radical formers or surface cross-linking molecules are applied, the reaction involving the additional use of radical formers and surface cross-linking molecules does not result in a direct covalent bond between two carbon atoms comprised in the backbone of two different polymer chains within the surface of a SAP particle. However, if radical formers and surface cross-linking molecules are additionally used, the reactions described above leading to a direct covalent bond will additionally take place.

Moreover, it is possible to use only radical formers, in which case carbon centered radicals in the polymer backbone are formed. In such embodiments, only direct covalent bonds are formed and the radical former is not covalently bonded to the surface of the SAP particles.

In embodiments using VUV, it is also possible to apply only surface cross-linking molecules without additionally using radical formers. In these embodiments, the carbon-centered radical formed in the polymer backbone comprised in the surface of a SAP particle upon VUV irradiation, reacts with one of the C=C double bonds of the surface cross-linking molecule. Thereby, the surface cross-linking molecule is covalently bound to the surface of the SAP particles and a radical is induced at one of the two C atoms, which have been comprised by the former C=C double bond of the surface cross-linking molecule. This radical is capable of abstracting again a hydrogen atom from another (neighboring) polymer chain within the surface of the SAP particle, thus resulting in another carbon-centered radical formed in the polymer backbone of this other polymer chain. This carbon centered radical can now react with the second C=C double bond comprised in the surface cross-linking molecule, which is already covalently bound to the SAP particle via the radical reaction, that has comprised the first C=C double bond. As a result, two polymer chains of the SAP particle are cross-linked via the reaction product of the surface cross-linking molecule.

The net reaction when using radical former molecules undergoing photo-fragmentation upon irradiation is the formation of a cross-link between two polymer chain segments, wherein the cross-link comprises the reaction product of one cross-linking molecule with two C=C double bonds and two radical former molecules.

With the additional use of surface cross-linking molecules the efficiency of the reaction can be further enhanced due to shorter reaction times: Without wanting to be bound by theory, it is believed that the rate determining step of a UV irradiation initiated surface cross-linking reaction in the absence of surface cross-linking molecules is the recombination of two carbon-centered radicals, forming a direct covalent bond between two carbon atoms comprised in two different polymer chains. This recombination follows a kinetic law of a second order, i.e. the reaction rate is proportional to the concentrations of both reactants (i.e. the two combining carbon-centered radicals) multiplied with each other.

If, however, surface cross-linking molecules are added, it is believed, that the reaction between the radical formed from the surface cross-linking molecule and the carbon-centered radical comprised in the polymer chain follows a kinetic law of pseudo-first order, i.e. the reaction rate is only proportional to the concentration of the carbon-centered radical, since the concentration of the second reaction partner, i.e. the radicals formed from the surface cross-linking molecule, is so high that it can be regarded as constant throughout the reaction. Reactions of pseudo-first order kinetics are known to be kinetically favored versus reactions of second order kinetics, i.e. they have a higher reaction speed.

Alternatively to radical former molecules undergoing photo-fragmentation it is also possible to use radical former molecules undergoing photo-reduction upon irradiation comprise carbonyl groups. In preferred embodiments of the present invention, such radical former molecules are ketones.

Upon UV irradiation, the radical former molecules of this type are transferred in an "excited state" (triplet state). Hence, they are not yet transformed into a radical, but are much more reactive than prior to irradiation.

In the next step, the radical former molecule in its excited state reacts with an aliphatic C—H group comprised in the backbone of a polymer chain in the surface of the SAP particle and abstracts a hydrogen radical, thereby forming a carbon-centered radical at this polymer chain and a ketyl radical.

The ketyl radical can now react with one of the C=C double bonds of the cross-linking molecule. Alternatively (or exclusively in embodiments which do not use surface cross-linking molecules) two ketyl radicals can recombine with one another to form a so-called pinacol, e.g. benzpinacol, for benzophenone as initiator.

In preferred embodiments of the present invention—for both types of radical former molecules—the cross-linking molecules comprise more than two C=C double bonds. In these embodiments, more than two polymer chain segments can be cross-linked to each other, following the reaction mechanism described above. In these embodiments, the number of reaction products of radical former molecules comprised by the cross-link equals the number of C=C double bonds comprised by the cross-linking molecule.

According to the present invention, only one type of cross-linking molecules may be used or, alternatively, two or more chemically different cross-linking molecules can be applied. Likewise, the only one type of radiation activatable radical former molecule can be used or, alternatively, two or more chemically different radiation activatable radical former molecules can be applied.

To ensure that SAP particles with evenly distributed surface cross-linking are obtained, the radical former (optionally applied if VUV is used, mandatory for all other UV radiation) and the optional surface cross-linking molecules have to be distributed evenly on the SAP particle. Therefore, the surface cross-linker is preferably applied by spraying onto the SAP particles.

Compared to the surface cross-linking known from the prior art, the surface cross-linking according to the present invention is significantly faster. Prior art surface cross-linking reactions carried out under increased temperatures commonly take up to 45 minutes. This time consuming process step renders the manufacturing process of SAP particles less economic than desirable. In contrast, the cross-linking process according to the present invention can be carried out within a significantly shorter reaction time, typically within minutes, and hence, enables an overall improvement with respect to manufacturing times of the SAP particles. This results in lower energy costs and higher throughput.

Furthermore, as the surface cross-linking reaction proceeds quickly, the radical former molecules (optionally applied if VUV is used) and—optionally—surface cross-linking molecules applied on the surface of the SAP particles have less time to penetrate inside the SAP particles. Hence, compared to prior art surface cross-linking, it is easier to actually restrict surface cross-linking to the surface of the SAP particles and to avoid undesired further cross-linking reactions in the core of the SAP particles.

Another advantage of the present invention refers to the neutralization step: $\alpha,\beta$-unsaturated carboxylic acid monomers are often neutralized prior to the polymerization step (pre-neutralization). Compounds, which are useful to neutralize the acid groups of the monomers, are typically those, which will sufficiently neutralize the acid groups without having a detrimental effect on the polymerization process. Such compounds include alkali metal hydroxides, alkali metal carbonates and bicarbonates. Preferably, the material used for neutralization of the monomers is sodium- or potassium-hydroxide, or sodium- or potassium-carbonate. As a result, the carboxyl groups comprised by the $\alpha,\beta$-unsaturated carboxylic acid of the polymer are at least partially neutralized. In case sodium hydroxide is used, neutralization results in sodium acrylate, which dissociates in water into negatively charged acrylate monomers and positively charged sodium ions. As the surface cross-linkers known in the art react with the carboxyl groups of the polymer, the degree of neutralization has to be balanced with the need to surface cross-link, because both process steps make use of the carboxyl groups.

If the final SAP particles are in the swollen state, after they absorbed aqueous solution, the sodium ions are freely movable within the SAP particles. In absorbent articles, such as diapers or training pants, the SAP particles typically absorb urine. Compared to distilled water, urine comprises a relatively high amount of salt, which at least partly is present in dissociated form. The dissociated salts comprised by the urine make absorption of liquid into the SAP particles more difficult, as the liquid has to be absorbed against an osmotic pressure caused by the ions of the dissociated salts. The freely movable sodium ions within the SAP particles strongly facilitate the absorption of liquid into the particles, because they reduce the osmotic pressure. Therefore, a high degree of neutralization can largely increase the capacity of the SAP particles and the speed of liquid absorption.

Furthermore, a higher degree of neutralization typically reduces the materials expenses and, consequently, also reduces the overall manufacturing costs for SAP particles: Sodium hydroxide, which is commonly used to neutralize the polymer, is typically less expansive compared to acrylic acid, which is the most preferred polymer of today's SAPs. Hence, increasing the neutralization degree increases the amount of sodium hydroxide comprised by a given amount of SAP. Consequently, less acrylic acid is required for making SAPs. Therefore, the method of the present invention provides an economical attractive way of making SAP particles.

A still further advantage of the present invention is the reduction of undesired side-reactions during the surface cross-linking process. Surface cross-linking known in the prior art requires increased temperatures, commonly around or above 150° C. At these temperatures, not only surface cross-linking is achieved, but also a number of other reactions take place, e.g. anhydride-formation within the polymer or dimer cleavage of dimers previously formed by the acrylic acid monomers. These side-reactions are highly undesired, because they result in SAP particles with decreases capacity.

As the surface cross-linking process according to the present invention does not necessarily need increased temperatures but can also be carried out at moderate temperatures, those side-reactions are considerably reduced. According to the present invention, the surface cross-linking reaction can preferably be accomplished at temperatures of less than 100° C., preferably at temperatures less than 80° C., more preferably at temperatures less than 50° C., even more preferably at temperatures less than 40° C., most preferably at temperatures between 20° C. and 40° C. Drying of the SAP may be carried out at temperatures above 100° C. but below 150° C., preferably below 120° C., to avoid the undesired side reactions.

Also, at elevated temperatures around or above 150° C. commonly applied in the surface cross-linking process known in the prior art, the SAP particles sometimes change their color from white to yellowish. Due to the reduced temperatures required for surface cross-linking in the method of the present invention, the problem of color degradation of the SAP particles can be considerably reduced.

The surface cross-linking according to the method of the present invention can optionally, though not preferably, be carried out together with one or more thermally activatable surface cross-linkers known in the art, e.g. 1,4-butandiol. In this case, however, both, UV radiation and increased temperatures (typically above 140° C.), are required. In these embodiments, the surface of the resulting SAP particles will further comprise the reaction product of the thermally activatable surface cross-linker.

In embodiments, wherein radical formers and/or surface cross-linking molecules are applied, the method of the present invention may further comprise an optional washing step to wash off un-reacted surface cross-linking molecules and/or radical former molecules or to wash off molecules formed by side reactions.

UV Irradiation

In the present invention, the SAP particles are exposed to ultraviolet-(UV-)radiation. The UV-domain of the electromagnetic spectrum is defined between wavelengths of 100 and 380 nm and is divided into the following ranges: UV-A (315 nm-400 nm), UV-B (280 nm-315 nm), UV-C (200 nm-280 nm) and Vacuum UV (VUV) (100 nm-200 nm).

Use of VUV Radiation:

Preferably, xenon ($Xe_2$-) excimer radiation sources, pulsed or continuous, are applied. In contrast to well-known excimer lasers, excimer lamps emit quasi-monochromatic incoherent radiation. Generation of incoherent excimer radiation is made possible for example by microwave discharges or by dielectrically barrier discharges (DBD, silent discharges) in specific gas atmospheres.

The preferred $Xe_2$-emission shows a relatively broad band in the VUV spectral domain from 160 to 200 nm, peaking at a wavelength of 172 nm with a full width at half maximum (FWHM, half-width) of 14 nm. The preferred wavelength within the VUV spectrum for use in the method of the present invention is from 160 nm to 200 nm, more preferred the wavelength has a peak at 172 nm.

A pulsed $Xe_2$-excimer radiation source suitable for laboratory studies is available under the trade name Xeradex™ (Osram, Munich, Germany) with electrical powers of 20 W or 100 W. However, if the method of the present invention is used to surface cross-link SAP particles in amounts common in industrial application, the power of the radiation source should be as high as 10 kW or even higher.

Continuous $Xe_2$-excimer radiation sources with electrical powers of up to 10 kW can be purchased from Heraeus Noblelight, Hanau, Germany), smaller sources are also available from Ushio Ltd. (e.g. Ushio Deutschland, Steinhöring).

Use of UV Radiation Having a Wavelength from 201 nm to 400 nm:

UV radiation within the UV-A, UV-B or UV-C range depending on the presence, concentration and nature of a photo-initiator, commercially available mercury arcs or metal halide radiation sources can be used. The choice, of the radiation source depends on the absorption spectrum of the radical initiator and possibly on geometry of the equipment used for surface cross-linking. The UV-B range proved to be most favorable in the present invention, in combination with the preferred afore-described initiators. The radiation sources can be optionally cooled with gas, and, to this end, may be embedded in or may contain a cooling sleeve.

The method of the present invention may be carried out in a fluidized bed reactor having a radial symmetric geometry with a rod-shaped radiation source in the centre or by using vibrating plates for UV exposure.

However, for the method of the present invention, the Brønsted acids and—if applicable—the radical formers and surface cross-linking molecules have to be homogeneously applied onto the SAP particles. Further, it has to be ensured that all SAP particles are homogeneously exposed to the UV radiation, avoiding that individual SAP particles are shadowed for an overly long period. Hence, the SAP particles have to be agitated while exposed to UV radiation, which may be done e.g. by rather gentle shear movements or by more vigorous agitation.

If VUV radiation is used for the method of the present invention, the method of the present invention is preferably carried out under normal atmosphere to reduce costs. However, as under normal atmosphere VUV radiation is partly absorbed by oxygen, the range of coverage of the VUV radiation is restricted. Moreover, upon absorption of VUV by oxygen, ozone is formed. Hence, it may be desirable to place the process equipment into a, preferably ventilated, container to avoid contact of operating personnel with ozone.

However, to increase the range of coverage of the VUV radiation (as the radiation is not absorbed by oxygen), the method of the present invention can also be carried out under nitrogen. The range of coverage of VUV in nitrogen is much larger compared to the range of coverage of VUV in normal atmosphere. This allows for more leeway in equipment design and process layout.

Also, high degrees of atmospheric humidity should be avoided, as VUV radiation is also absorbed by water molecules, and the degree of atmospheric humidity should be kept substantially constant over time to achieve a relatively constant degree of surface cross-linking. To control the degree of atmospheric humidity and to restrict atmospheric humidity to a relatively low level, the water content in the SAP particles should be kept constant, preferably at a relatively low level.

If UV radiation having a wavelength from 201 nm to 400 nm is used for the method of the present invention, it is preferred that the method of the present invention is carried out under normal atmosphere to reduce costs. Also, without wishing to be bound by theory, it is believed that normal atmosphere enables improved surface cross-linking results as oxygen, which is a bi-radical, may participate in the reaction mechanism by formation of intermediate peroxile radicals upon irradiation. Hence, the number of available radicals is proliferated, which in turn enable the formation of carbon-centered radicals in the polymer backbone of the polymer chains in the surface of the SAP particles. The degree of humidity is not crucial for UV irradiation having a wavelength from 201 nm to 400 nm, as water molecules do not absorb within that range.

Brønsted Acids

For surface cross-linking with UV irradiation, using SAP particles with a relatively high degree of neutralization, Brønsted acids are able to considerably improve the surface cross-linking process.

In the method of the present invention, SAP particles with degrees of neutralization of 60 mol-% or above, namely from 60 mol-% to 95 mol-%, more preferably from 65 mol-% to mol-95 mol-%, even more preferably from 70 mol-% to 95 mol-% and most preferably from 75 mol-% to 95 mol-% are subjected to UV irradiation for surface cross-linking. To improve the effectiveness of the method, Brønsted acids are applied onto the SAP particles.

It is believed that the electron-drawing effect (known in the literature as "-I effect") of the carboxyl groups (COOH) comprised by the polymer of the SAP particles contributes to the overall reaction speed and efficiency of the surface cross-linking method of the present invention, though they are not directly involved in the surface cross-linking reactions (see above). This is presumably due to an accelerated hydrogen abstraction from C—H groups positioned adjacent the carboxyl groups in the backbone of the polymer, which results in the formation of carbon-centered radicals in the backbone of the polymer (see above).

However, for SAP particles having a relatively high degree of neutralization, most of the carboxyl group are de-protonated ($COO^-$), as they are in the form of the corresponding carboxylate salt (COOM with M being a monovalent metal cation such as $Na^+$). The "-I effect" of the carboxylate salt is known to be weaker compared to the protonated form. It has been found that this shortcoming of SAP particles with a relatively high degree of neutralization in light of surface cross-linking with UV radiation can be compensated by adding a Brønsted acid without affecting the overall concept of neutralization. The Brønsted acid is capable of releasing protons ($H^+$), thereby transferring the carboxylate salt in the surface of the SAP particle into the protonated form COOH.

Also, if the carbon-centered radical in the backbone of the polymer comprised by the SAP particle is formed by decarboxylation, i.e. by abstracting a whole carboxyl group instead of abstracting a proton from a C—H group, the increased number of protonated COOH groups in the surface of the SAP particles positively influences the effectiveness of surface cross-linking with UV radiation: COOH groups undergo significantly more readily decarboxylation than COOM groups By subjecting SAP particles with a relatively high degree of neutralization to a treatment with one or more Brønsted acids, a low degree of neutralization can be selectively adjusted in the surface of the SAP particles, resulting in a more efficient reaction. At the same time, these SAP particles still to have a relatively high degree of neutralization in the core of the SAP particles, which is economically favorable due to the advantages of a high neutralization degree as described above.

Additionally to the Brønsted acid, a Lewis acid can be applied, preferably the aluminum cation $Al^{3+}$, wherein $Al^{3+}$ is preferably applied in the form of aluminum sulfate $Al_2(SO_4)_3$.

A Brønsted acid is any organic or inorganic compound capable of releasing protons ($H^+$). Preferred Brønsted acids for the present invention are mineral acids like hydrochloric acid, sulphuric acid, phosphoric acid; saturated organic carboxylic acid like acetic acid, lactic acid, citric acid, succinic acid; oligomeric or polymeric organic acids like low molecular weight poly acrylic acid having a molecular weight of from 50 to 5000 g/mol and saturated inorganic acids. A preferred saturated inorganic acid for use in the present invention is boric acid. The most preferred Brønsted acids according to the present invention are the mineral acids and the saturated organic carboxylic acids with the mineral acids being even more preferred than the carboxylic acids. According to the present invention, hydrochloric acid is the most preferred Brønsted acid.

The $pK_a$ value (dissociation index) of the Brønsted acid should be lower than the $pK_a$ value of the conjugated acid of the SAP repeat unit, which—in case of poly(meth)acrylic acid as polymer in the SAP particle—is typically between 4 and 5. Brønsted acids applied in the method of the present invention preferably have a $pK_a$ value of less than 5, more preferably less than 4 and most preferably less than 3. For example, HCl, which is the most preferred Brønsted acid for use in the present invention, has a $pK_a$ value of −6.

However, apart from the pKa value, the effect of the acid on the particle flow behavior of the SAP particles during the irradiation may also influence the Brønsted acid, which is finally selected for the method of the present invention. Some Brønsted acids may result on agglomeration of the SAP particles while other may even have a positive effect on the fluidity properties of the SAP particles (and may thus act as fluidity enhancers). The selection of the appropriate Brønsted acid therefore may have to be made depending on the given circumstances.

The amount of the Brønsted acid applied in the method of the present invention is preferably in the range of from 0.005 weight-% to 10 weight-% by weight of SAP particles, more preferably from 0.01 weight-% to 5.0 weight-% and most preferably from 0.1 weight-% to 3.0 weight-%. The amount of Brønsted acid also depends on the Brønsted acid which is used, on the radical former (if applied) and on the surface cross-linking molecules (if applied). Generally, if a relatively weak Brønsted acid or a Brønsted acid with a relatively high molecular weight is applied, the amount of Brønsted acid should be higher compared to a stronger Brønsted acid or to a Brønsted acid having a lower molecular weight. Also, Brønsted acids having a lower $pK_a$ value will be required in lower amounts compared to a Brønsted acid with a higher $pK_a$ value. HCl, as the most preferred Brønsted acid, is preferably applied in the range of from 0.1 weight-% to 1.0 weight-% by weight of the SAP particles.

In principle, also a mixture of several Brønsted acids can be used. However, this is less preferred as it increases the overall complexity of the method.

The Brønsted acid is preferably applied in water as an aqueous solution, as an emulsion or a suspension, which preferably also comprises the UV activatable radical former and the surface cross-linking molecules (if applied). A typical concentration of the Brønsted acid in an aqueous solution is 1 mol/l to 2 mol/l. Alternatively, the Brønsted acid can also be applied separately from the radical former and/or surface cross-linking molecules (if applied).

Also, the Brønsted acids can be applied while dissolved or suspended in alcohol, e.g. isopropanol. The advantage of using alcohol instead of water is that alcohol does not migrate into the SAP particles to a substantial degree. Hence, it is easier to control the penetration depth in order to avoid Brønsted acids migrating onto the core. Thereby it is easier to ensure that the surface cross-linking reaction is actually restricted to the surface of the SAP particles. The alcohol may be removed (via evaporation) prior to UV irradiation of the SAP particles.

If the Brønsted acids are applied in a mixture of alcohol and water, the penetration depth of the mixture—and thereby of the Brønsted acids—can be carefully adjusted by choosing the appropriate ratio between alcohol and water.

It may also be desirable to apply the Brønsted acid suspended in water, choosing a Brønsted acid which does not dissolve in water very well. Thereby it is also possible to ensure that the Brønsted acids actually remain in the surface of the SAP particles and do not migrate into the core together with the water.

The Brønsted acid can be applied onto the SAP particles prior to UV irradiation. If the Brønsted acid is applied in water, it is preferred that it is applied immediately before UV irradiation takes place to ensure that the Brønsted acid does not migrate into the core to a substantial degree. Preferably, the Brønsted acid should not be applied more than 10 min prior to UV irradiation, more preferably not more than 5 minutes and most preferably the time between application of the Brønsted acid and UV irradiation should not be more than 1 minute, especially if the Brønsted acid is applied in water.

As the SAP particles have a buffering effect for the Brønsted acid, it may be desirable to apply the Brønsted acid continuously during UV irradiation e.g. via spraying to ensure a permanent surplus of Brønsted acid. The Brønsted acid can be applied continuously during UV irradiation in addition to an initial application of Brønsted acid prior to UV irradiation or can be applied only during UV irradiation.

Fluidity enhancers, as they are widely known in the art, such as hydrophilic amorphous silicas, as they are commercially available e.g. from Degussa Corp., can optionally be added to the SAP particles to assist in avoiding agglomerates, e.g. if the water content of the SAP particles is relatively high. The fluidity enhancers are typically applied in a range of from 0.1 weight-% by weight of SAP particles to 10 weight-% by weight of SAP particles.

Applications

The SAP particles made by the method of the present invention are usable for sanitary cotton, disposable diapers, and other sanitary materials for absorbing body fluid and for agricultural activities, preferably applied in absorbent cores of absorbent articles.

Test Methods

The capacity of the SAP particles is often described in terms of the centrifuge retention capacity value (CRC). A test method for CRC is described in EDANA method 441.2-02.

The parameter commonly used to describe the behavior of SAP particles under a certain pressure is AAP (absorbency against pressure). AAP is measured according to EDANA method 442.2-02, using a pressure of 4.83 kPa.

Permeability of the gel bed comprised of SAP particles is generally measured as saline flow conductivity (SFC). A test method to determine SFC is described in U.S. Pat. No. 5,562,646, issued to Goldman et al. on Oct. 8, 1996. For the present invention, the test method in U.S. Pat. No. 5,562,646 is modified in that a 0.9% NaCl solution is used instead of Jayco solution).

The absorbency against pressure (AAP) of 4.83 kPa of the superabsorbent polymer particles increases by at least 1 g/g after the superabsorbent polymer particles have been subjected to the method of the present invention.

The saline flow conductivity (SFC) of the superabsorbent polymer particles increases by at least $10 \times 10^{-7}$ cm$^3 \cdot$s$\cdot$g$^{-1}$ after the superabsorbent polymer particles have been subjected to the method of the present invention.

EXAMPLES

Base Polymer

As base polymer, the water-swellable polymer as described in Example 1.2 of WO 2005/014066 A1, titled "Absorbent articles comprising coated water-swellable material" and filed on 17 Feb. 2005 is used. However, the neutralization degree of the base polymer, which is 75 mol % in Example 1.2 of WO 2005/014066 A1 has been adjusted to 70 mol % and 85 mol %, respectively, as required by the Examples herein. Also, the amount of MBAA has to be routinely adjusted accordingly to obtain SAP particles with a CRC value of 30.5 g/g (Example 1) and 31 g/g (Example 2). It should be noted, that the CRC value can principally be adjusted in the same way as the CCRC way, which is described in Example 1.2 of WO 2005/014066 A1.

Example 1

3 parts of the radical former sodium peroxodisulfate, and 0.6 parts of the Brønsted acid HCl are dissolved in 7 parts of water.

100 parts (per weight) of non-surface cross-linked SAP particles consisting only of the base polymer described above and having a degree of neutralization of 70 mol % are mixed with the aqueous solution comprising the radical former sodium peroxodisulfate and the Brønsted acid HCl under vigorous stirring. Mixing is done for 10 minutes.

Immediately thereafter, the SAP particles are subjected to UV irradiation for 10 minutes, using a 2 kW Medium Pressure Mercury Lamp. The distance between the irradiation source and the SAP particles is as small as possible and in the current example is about 10 cm. The mixing continued throughout the irradiation step. Mixing and irradiation are carried out under normal atmosphere.

The 100 parts of SAP particles correspond to 10 g and the SAP particles have a particle size distribution of from 150 μm to 850 μm.

Comparative Example 1

Comparative example 1 corresponds to Example 1 with the only difference that no Brønsted acid has been added.

Example 2

Example 2 differs from Example 1 in that the SAP particles consisting only of the base polymer described above have a degree of neutralization of 80 mol %. Also, 8 parts of water have been added instead of 7 parts. Otherwise, Example 2 does not differ from Example 1.

Comparative Example 2

Comparative example 2 corresponds to Example 2 with the only difference that no Brønsted acid has been added.

The SFC, AAP and CRC values for these Examples are summarized in Table 1:

Example 3

Example 3 differs from Example 1 in that instead of applying HCl as Brønsted acid, 1.6 parts of the Brønsted acid $H_2SO_4$ are applied. Also, 8 parts of water have been added instead of 7 parts. Otherwise, Example 3 does not differ from Example 1.

The SFC, AAP and CRC value of the initial SAP particles consisting only of the base polymer (70 mol % neutralized and 85 mol % neutralized, respectively) and of the SAP particles of Examples 1, 2 and 3 and Comparative Examples 1 and 2 after they have been subjected to the test is determined according to the test methods set out above.

TABLE 1

| | UV surface cross-linking | Brønsted acid | Neutralization (mol %) | CRC (g/g) | AAP at 4.83 kPa (g/g) | SFC ($10^{-7}$ cm$^3$ s g$^{-1}$) |
|---|---|---|---|---|---|---|
| Base polymer | No | none | 70 | 30.5 | 6.9 | 0 |
| Example 1 | Yes | HCl | 70 | 24.8 | 19.5 | 64 |
| Comparative Example 1 | Yes | none | 70 | 26.2 | 18.9 | 24 |
| Example 3 | Yes | H$_2$SO$_4$ | 70 | 25.2 | 18.8 | 48 |
| Base polymer | No | none | 85 | 31.0 | 6.0 | 0 |
| Example 2 | Yes | HCl | 85 | 26.3 | 17.1 | 11 |
| Comparative Example 2 | yes | None | 85 | 27.1 | 13.2 | 3 |

For SAP particles without surface cross-linking (hence, only consisting of the base polymer), the CRC value is typically rather high as the SAP particles are not restricted in swelling due to the cross-links introduced on the surface of the SAP particles. After surface cross-linking, the CRC value of the SAP particles decreases.

Contrary thereto, the AAP and SFC values for non surface cross-linked SAP particles is very low (for the SFC, the value can be as low as zero): As the SAP particles are extremely soft, they easily deform under pressure (=low AAP value). Consequently, gel blocking occurs, which results in a very low SFC value.

Generally, an increase in AAP and SFC value and a decrease in CRC value compared to the non surface cross-linked SAP particles consisting only of the base polymer is an indirect proof that surface cross-linking has actually taken place.

Hence, the Examples show that the base polymer has indeed been surface cross-linked by the method of the present invention.

All documents cited in the Detailed Description of the Invention, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Each dimension for which a value is defined herein is a technical dimension, which in the context of the present invention is not to be understood literal. Hence, all embodiments having dimensions functionally equivalent to the dimensions stated herein are intended to be covered by the scope of the invention, e.g. a dimension of "40 mm" has to be understood as meaning "about 40 mm".

The invention claimed is:

1. A method of surface cross-linking superabsorbent polymer particles which comprises the steps of
   a) providing superabsorbent polymer particles having a surface and a core and having a degree of neutralization of more than 60 mol-%;
   b) applying one or more Brønsted acids in a concentration of 0.005-10% by weight of the superabsorbent polymer particles onto the surface of the superabsorbent polymer particles; and either
   c1) exposing said superabsorbent polymer particles to irradiation with vacuum UV radiation having a wavelength from 100 nm to 200 nm or
   c2) exposing said superabsorbent polymer particles to irradiation with UV radiation having a wavelength from 201 nm to 400 nm and wherein further to the Brønsted acids, a radical former molecule is applied to the surface of the superabsorbent polymer particles,
   to form surface cross-linked superabsorbent polymer particles;
   wherein the surface cross-linked superabsorbent polymer particles have a higher absorbency against pressure of 4.83 kPa than the superabsorbent polymer particles prior to being subjected to the method.

2. The method of claim 1 option c1), wherein further to the Brønsted acids, a radical former molecules is applied to the surface of the superabsorbent polymer particles.

3. The method of claim 1, wherein additionally a surface cross-linking molecule is applied to the surface of the superabsorbent polymer particles and wherein the surface cross-linking molecule comprises at least two functional groups, said functional groups being C=C double bonds or being CH—X moieties, with X being a hetero atom.

4. The method of claim 1 wherein the Brønsted acid is selected from the group consisting of hydrochloric acid, sulphuric acid and phosphoric acid.

5. The method of claim 1, wherein the Brønsted acid is applied continuously during UV irradiation of the superabsorbent polymer particles.

6. The method of claim 1, wherein said c1) or said C2) is carried out at temperatures of less than 100° C.

7. The method of claim 1, wherein the absorbency against pressure (AAP) of 4.83 kPa of the superabsorbent polymer particles increases by at least 1 g/g after the superabsorbent polymer particles have been subjected to the method.

8. The method of claim 1, wherein the saline flow conductivity (SFC) of the superabsorbent polymer particles increases by at least $10 \times 10^{-7}$ cm$^3$·s·g$^{-1}$ after the superabsorbent polymer particles have been subjected to the method.

9. The method of claim 2, wherein additionally a surface cross-linking molecule is applied to the surface of the superabsorbent polymer particles and wherein the surface cross-linking molecule comprises at least two functional groups, said functional groups being C=C double bonds or being CH—X moieties, with X being a hetero atom.

10. The method of claim 2, wherein the Brønsted acid is selected from the group consisting of hydrochloric acid, sulphuric acid and phosphoric acid.

11. The method of claim 3, wherein the Brønsted acid is selected from the group consisting of hydrochloric acid, sulphuric acid and phosphoric acid.

12. The method of claim 9, wherein the Brønsted acid is selected from the group consisting of hydrochloric acid, sulphuric acid and phosphoric acid.

13. The method of claim 1, wherein step c1) or c2) is carried out in the presence of a surface cross-linking molecule having at least two functional groups for reacting with a carbon-centered radical located in the backbone of a polymeric chain in the surface of the superabsorbent polymer particles obtained by step a).

14. The method of claim 13, wherein the surface cross-linking molecule is selected from the group consisting of triallyl cyanurate, triallyl isocyanurate, trimethylpropane triacrylate or other triacrylate esters, pentaerythritol triallyl ether, pentaerythritol tetraallyl ether, butanediol diacrylate, pentaerythritol tetraacrylate, tetra allylorthosilicate, di-pentaerythritol pentaacyralate, di-pentaerythritol hexaacyralate, ethyleneglycol diacrylate, ethyleneglycol dimethacrylate, tetra allyloxy ethane, diallyl phthalate, diethyleneglycol diacrylate, allylmethacrylate, triallylamine, 1,1,1-trimethylolpropane triacrylate, triallyl citrate, and triallyl amine.

15. The method of claim 1, wherein step c1) or c2) is carried out in the absence of the application of a surface cross-linking molecule.

* * * * *